US00PP29088P2

(12) United States Plant Patent
de Geus et al.

(10) Patent No.: US PP29,088 P2
(45) Date of Patent: Mar. 13, 2018

(54) SHRUB ROSE PLANT NAMED 'GEUS4310'

(50) Latin Name: ***Rosa* hybrid**
Varietal Denomination: GEUS4310

(71) Applicant: Select Breeding B.V., Klazienaveen (NL)

(72) Inventors: Dennis de Geus, Noord (NL); Michael de Geus, Barger-Compascuum (NL)

(73) Assignee: SELECT BREEDING B.V., Klazienaveen (NL)

( * ) Notice: Subject to any disclaimer, the term of this patent is extended or adjusted under 35 U.S.C. 154(b) by 0 days.

(21) Appl. No.: 15/330,254

(22) Filed: Aug. 30, 2016

(51) Int. Cl.
*A01H 5/02* (2006.01)

(52) U.S. Cl.
USPC ..... Plt./108

(58) Field of Classification Search
USPC ..... Plt./101, 102, 108
See application file for complete search history.

*Primary Examiner* — Susan McCormick Ewoldt
*Assistant Examiner* — Karen Redden
(74) *Attorney, Agent, or Firm* — Penny J. Aguirre

(57) ABSTRACT

A new cultivar of *Rosa* plant named, 'GEUS4310' that is characterized by its compact, upright, uniform plant habit, its double flowers that are deep reddish pink (cerise) in color, its smooth stems with few thorns, and its small leaves that remain healthy throughout the entire growing season.

2 Drawing Sheets

Botanical classification: *Rosa* hybrid.
Variety denomination: 'GEUS4310'.

BACKGROUND OF THE INVENTION

The present invention relates to a new and distinct cultivar of *Rosa* hybrid. The new cultivar will be referred to hereafter by its cultivar name, 'GEUS4310'. 'GEUS4310' is a new cultivar of shrub rose grown for use as a container and landscape plant.

The new cultivar of shrub rose is a selection from an ongoing controlled breeding program conducted by the Inventors in Klazienaveen, The Netherlands. The objectives of the breeding program are to develop improved cultivars of shrub rose with increased plant health, compact growth habits, and multiple blooms of large flowers during the growing season.

'GEUS4310' was derived from a controlled cross made in June of 2010 between *Rosa* cultivars 'Jaap Stamroos' (not patented) as the female parent and 'Poulman' (U.S. Plant Pat. No. 6,264) as the male parent. 'GEUS4310' was selected in May of 2012 as a single unique plant amongst the resulting seedlings from the above cross.

Asexual propagation of the new cultivar was first accomplished by softwood stem cuttings by one of the Inventors in May of 2012 in Klazienaveen, The Netherlands. Asexual propagation by softwood stem cuttings has determined that the characteristics of this cultivar are stable and reproduced true to type in successive generations.

SUMMARY OF THE INVENTION

The following traits have been repeatedly observed and represent the characteristics of the new cultivar. These attributes in combination distinguish 'GEUS4310' as a unique cultivar of *Rosa*.

1. 'GEUS4310' exhibits a compact, upright, and uniform plant habit.

2. 'GEUS4310' exhibits double flowers that are deep reddish pink (cerise) in color.
3. 'GEUS4310' exhibits smooth stems with few thorns.
4. 'GEUS4310' exhibits small leaves that remain healthy throughout the entire growing season.

The female parent of 'GEUS4310', 'Jaap Stamroos', differs from 'GEUS4310' in having flowers that are redder in color, in having flower buds that are smaller in size, in having more flower buds per plant, and in having leaves that are smaller in size. The male parent of 'GEUS4310', 'Poulman', differs from 'GEUS4310' in being a hybrid tea rose, in having flowers that are more red in color, in having flower buds that are larger in size, and in having fewer flower buds per plant. 'GEUS4310' can also be compared to the *Rosa* cultivars 'Peajumbo' (not patented) and 'KORfloci24' (U.S. Plant Pat. No. 23,353). 'Peajumbo' is similar to 'GEUS4310' in having flower buds that are ovate in shape and in having a similar overall plant height. 'Peajumbo' differs from 'GEUS4310' in having flowers that are more red in color, in having leaves and sepals that are larger in size, in having leaves that are olive green in color, and in being a less healthy plant overall. 'KORfloci24' is similar to 'GEUS4310' in number of flowers per lateral stem. 'KORfloci24' differs from 'GEUS4310' in having flowers that are pink and yellow in color, in having flower buds that are globose in shape, and in being a less healthy plant overall.

BRIEF DESCRIPTION OF THE DRAWINGS

The accompanying colored photographs illustrate the overall appearance and distinct characteristics of the new *Rosa*. The photographs were taken of a one year-old plant of 'GEUS4310' as grown in a greenhouse in a 2-gallon container in Salem, Oregon.

The photograph in FIG. 1 provides a side view of a plant of 'GEUS4310' in bloom.

Figure 1:
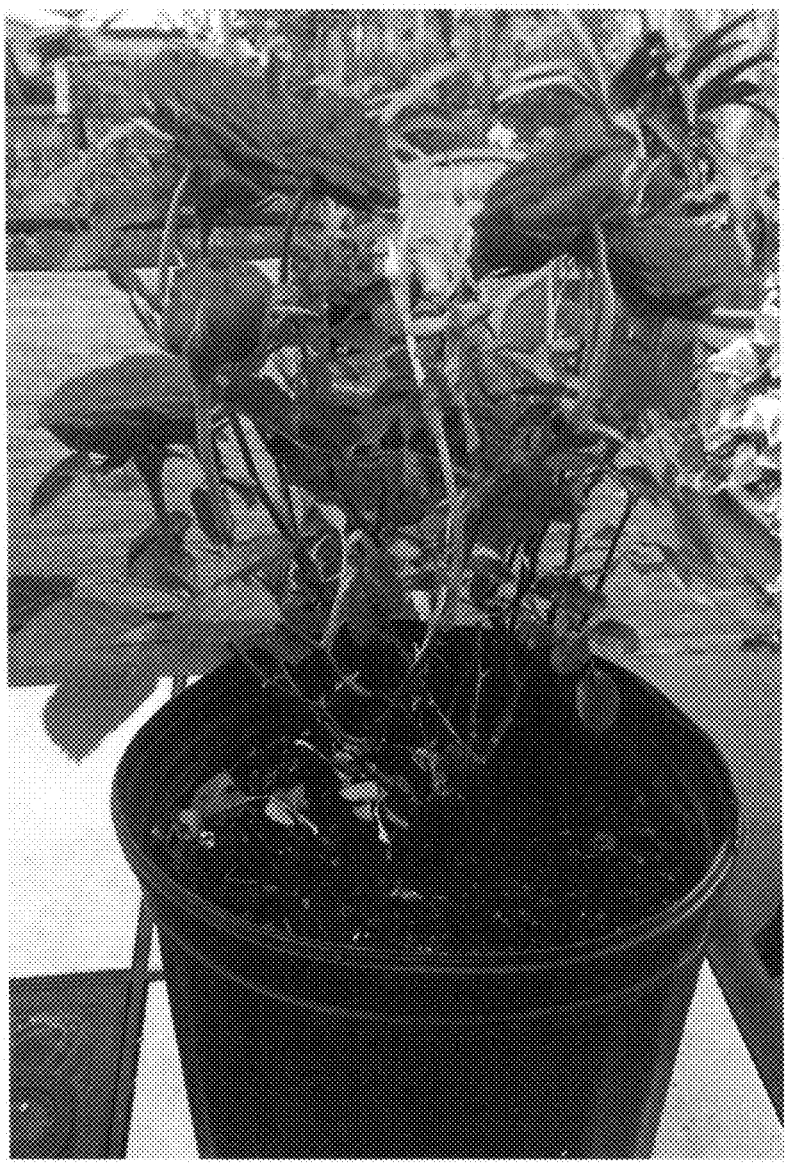
Figure 2:
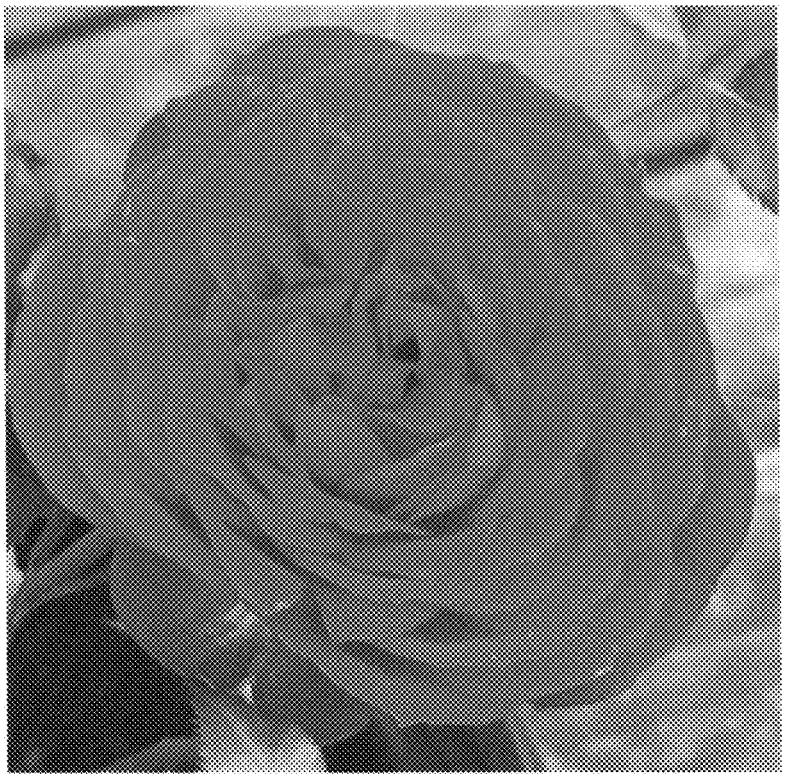

The photograph in FIG. 2 provides a close-up view of a flower of 'GEUS4310'.

Figure 3:
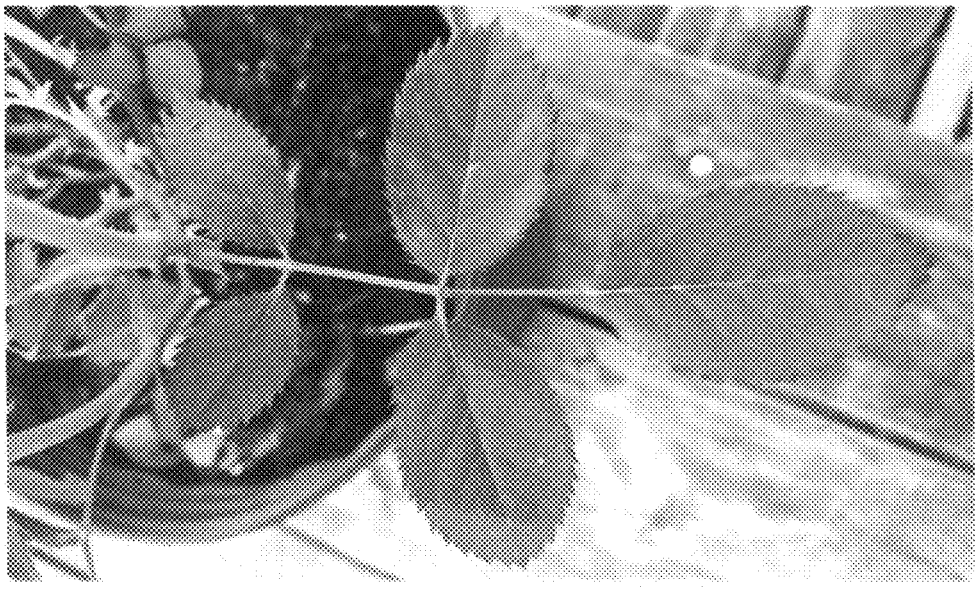

The photograph in FIG. 3 provides a close-up view of the foliage of 'GEUS4310'.

The colors in the photographs are as close as possible with the photographic and printing technology utilized and the color values cited in the Detailed Botanical Description accurately describe the colors of the new *Rosa*.

DETAILED BOTANICAL DESCRIPTION

The following is a detailed description of one year-old plants of 'GEUS4310' as grown in a greenhouse in 2-gallon containers in Salem, Oreg. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming habit.*—From June to September in The Netherlands.

*Plant type.*—Herbaceous perennial.

*Plant habit.*—Compact, upright and uniform.

*Height and spread.*—An average of 60 cm in height and 40 cm in spread.

*Cold hardiness.*—At least to U.S.D.A. Zone 8.

*Diseases.*—Plant have been observed to healthy and free from diseases such as rose black spot (*Diplocarpon rosae*) and rose powdery mildew (*Podosphaera pannosa*).

*Root description.*—Fibrous and fine, 161B to 161D in color.

*Root development.*—An average of 90 days for root initiation with a young rooted plant in a 72-cell liner produced in 30 days from a rooted cutting.

*Propagation*—Softwood stem cuttings.

*Growth rate.*—Moderate.

Branch description:

*Stem shape.*—Rounded.

*Stem color.*—Young and mature stems; 143A to 143C with mature wood; 177D.

*Stem surface.*—Young and mature stems; glabrous and smooth, mature wood; glabrous and finely barked.

*Stem size.*—Main branches; an average of 5 mm in width and 2.5 cm in length, lateral branches; an average of 4 mm in width and 3.5 cm in length, secondary branches; an average of 2.7 mm in width and 15 cm in length.

*Branching.*—Well-branched, an average of 3 main branches, 3 lateral branches per main branch, and 3 secondary branches per lateral branch.

*Thorns.*—Sparsely distributed with an average of one per branch when present, elongated triangle in shape, held outward to slightly downwards, oval base, entire margin, narrowly acute apex, an average of 3.5 mm in length with a base 1.5 mm in length and 1 mm in width, 162D in color.

Foliage description:

*Leaves.*—Odd-pinnate division, alternate arrangement, an average of 6 cm in length and 4.8 cm in width, internode length is an average of 3 cm.

*Leaflets.*—An average of 3 to 5, oval in shape, rounded base, acute apex, serrate margins, apical leaflet; an average of 3 cm in length and 1.9 cm in width, lateral leaflets; an average of 2.3 cm in length and 1.5 cm in width, color; young and mature leaves upper and lower surfaces a blend between 138A and 143A, veins; pinnate, inconspicuous and 138B in color, upper surface; glabrous, smooth, and glossy, lower surface; glabrous, smooth, and dull.

*Rachis.*—An average of 2 cm in length and 1 mm in diameter, color; upper surface 143A and lower surface 144B to 144C, glabrous and smooth upper and lower surface.

*Stipules.*—Held outward with auricle facing outward, adnate to petiole, an average of 1.4 cm in length and 1.7 mm in width, color upper and lower surface; 143A to 143C, lighter in color near the center, both surfaces glabrous and smooth.

*Petioles and petiolules.*—Petioles; an average of 2 cm in length and 1 mm in width, apical petiolules; an average of 1.1 cm in length and 1 mm in width, lateral petiolules; an average of 2 mm in length and 1 mm in width, petioles and petiolules; color upper surface 143A and lower surface 144B to 144C, both surfaces glabrous and smooth.

Inflorescence description:

*Inflorescence type.*—Solitary rosette-formed double flowers present at the stem apices.

*Flower number.*—An average of 1 per lateral stem.

*Flower fragrance.*—Light pleasant, sweet rose scent.

*Flower longevity.*—10 to 12 days, depending on temperature and sunlight exposure.

*Flower type.*—Double solitary symmetrical round rosettes.

*Flower size.*—An average of 4 cm in diameter and 1.8 cm in depth.

*Flower aspect.*—Upwards and outwards.

*Peduncles.*—Round in shape, an average of 4 cm in length and 2.1 mm in diameter, glabrous and glossy surface, 144A in color.

*Bracts.*—None observed.

*Flower buds.*—Ovate in shape, an average of 2.5 cm in length and 1.5 cm in width prior to opening, color N66B to N66C.

*Sepals.*—5, lanceolate in shape, entire margin often with 2 very fine leafy appendages about 5 mm in length present, acuminate apex, truncate base, an average of 1.8 cm in length and 7 mm in width color; upper and lower surfaces 143A with 145A at the center, margin appears NN155D due to pubescence, reflexed towards stem, both surfaces dull and pubescent, with increased pubescence towards the margin.

*Petals.*—An average of 75 per flower, obovate in shape, entire margin, cuneate base, rounded apex with outer petals retuse, outer petals; an average of 2 cm in length and 1.5 cm in width, inner petals; an average of 1.3 cm in length and 7 mm in width, color; opening and fully open upper and lower surfaces; N66A with very base a blend between 150D and N155C, glabrous, smooth, and velvety upper and lower surfaces.

*Receptacle.*—An average of 6 mm in diameter and 2 mm in depth when flower is fully open, waxy surface, 145A in color.

Reproductive organs:

*Gynoecium.*—About 50 pistils per flower, stigma; an average of 1 mm in length, a mix of 11C and N66A in color, style; an average of 2 mm in length and 0.7 mm in width, a blend between 142D and 157A in color, ovary is narrow oblong in shape, an average of 2 mm in length and 1 mm in width, NN155C in color.

*Androcoecium.*—An average of 80 stamens, filaments; an average of 3.5 mm in length and blend of 13B in color, basifixed anthers; an average of 2 mm in length and 1 mm in width, and 13A with 11B at the center in color, pollen is low in quantity and 23B in color.

*Hips.*—None observed to date.

It is claimed:

1. A new and distinct cultivar of *Rosa* plant named 'GEUS4310' as herein illustrated and described.

* * * * *